Commercialized Sulfonylurea Herbicides

United States Patent [19]
Grandoni
[11] Patent Number: 5,998,420
[45] Date of Patent: Dec. 7, 1999
[54] METHOD FOR TREATING *MYCOBACTERIUM TUBERCULOSIS*
[75] Inventor: Jerry Grandoni, Haddonfield, N.J.
[73] Assignee: University of Medicine & Dentistry of New Jersey, Newark, N.J.
[21] Appl. No.: 08/629,241
[22] Fil

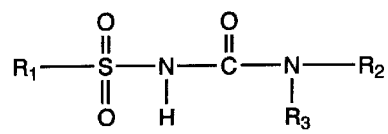

1

| Common Name | $R_1 - R_2 - R_3$ | Common Name | $R_1 - R_2 - R_3$ |
|---|---|---|---|
| amidosulfuron | K - S - Hy | nicosulfuron | H - S - Hy |
| bensulfuron | O - S - Hy | primisulfuron | A - U - Hy |
| chlorimuron ethyl | F - V - Hy | pyrazosulfuron ethyl | N - S - Hy |
| chlorsulfuron | Q - R - Hy | | |
| cinosulfuron | I - Y - Hy | rimsulfuron | G - S - Hy |
| ethametsulfuron methyl | A - W - Hy | sulfometuron methyl | A - T - Hy |
| flazasulfuron | B - S - Hy | thifensulfuron | L - R - Hy |
| halosulfuron | E - S - Hy | triasulfuron | P - R - Hy |
| imazosulfuron | M - S - Hy | tribenuron | A - R - Me |
| metsulfuron methyl | A - R - Hy | triflusulfuron | C - X - Hy |
| | | CGA-152005 | D - R - Hy |
| | | NC-330 | J - R - Hy |

Figure 3

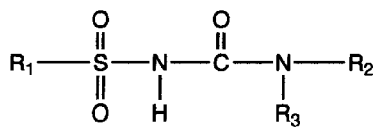
1
R$_2$:
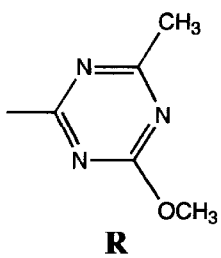
R
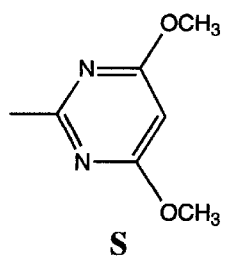
S
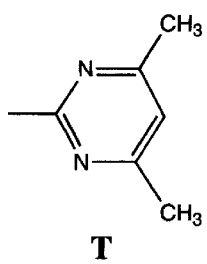
T
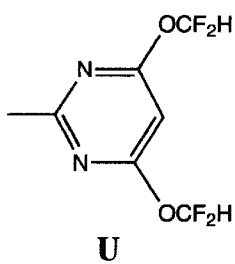
U
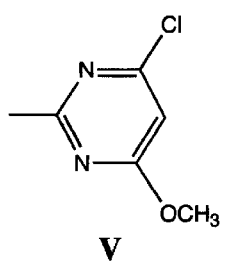
V
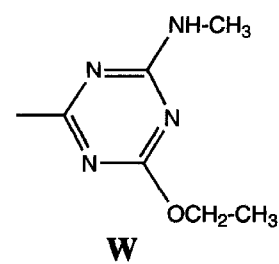
W
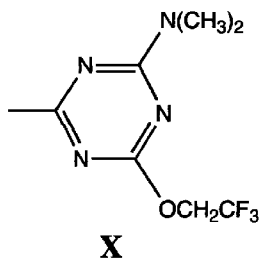
X
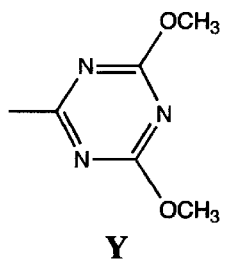
Y
R$_3$:  —H  or  —CH$_3$
Hy      Me
Figure 5

Imidazolinone Herbicides
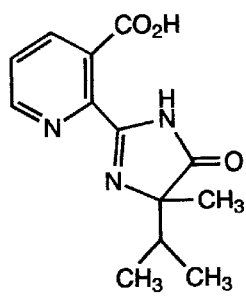
2 imazapyr
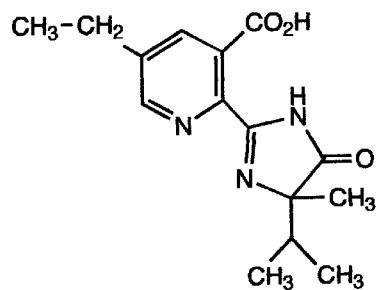
3 imazethapyr
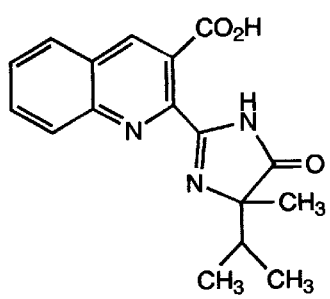
4 imazaquin
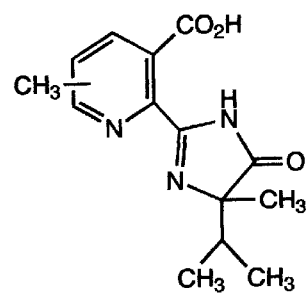
5 imazamethabenz methyl
Triazolopyrimidine Sulfoanilide Herbicides
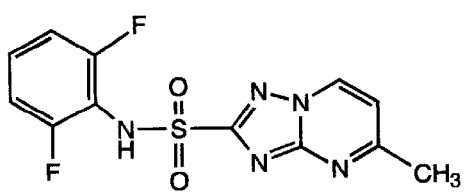
6 flumetsulam
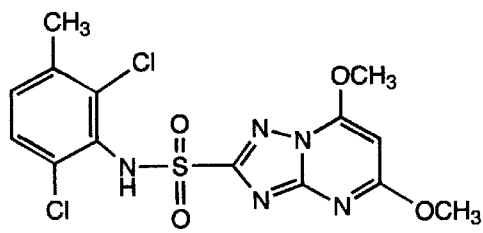
7 metosulam
Pyrimidyloxy Salicylic Acid Herbicides
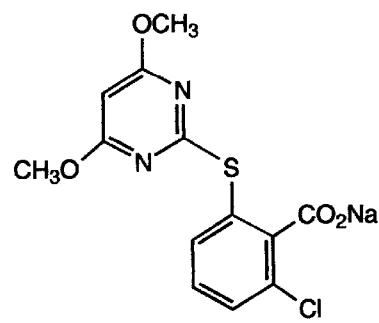
8 KIH-2031/DPX-PE 350
Figure 6

Oxalyl Hydroxamates
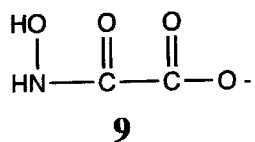
9
N-Substituted
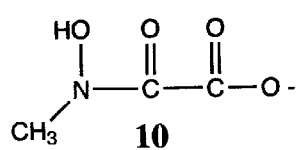
10
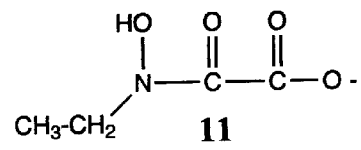
11
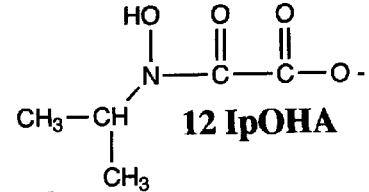
12 IpOHA
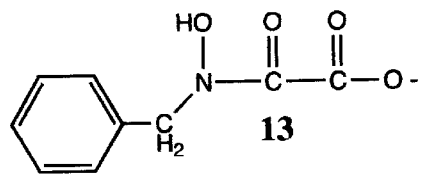
13
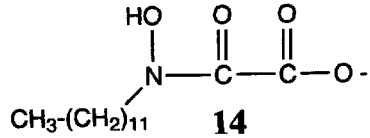
14
O-Substituted
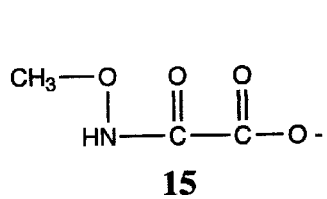
15
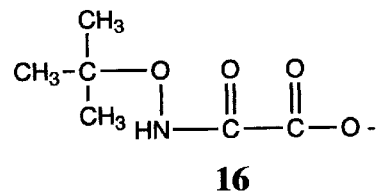
16
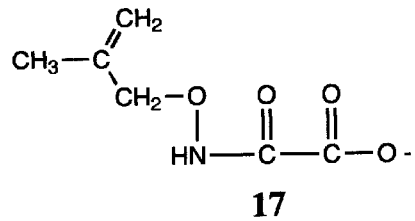
17
Phosphinic Acids
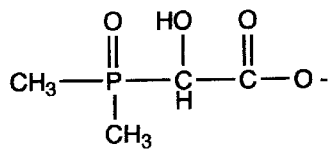
18 Hoe 704
Nitronates
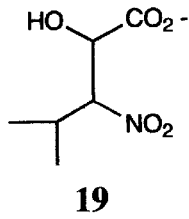
19
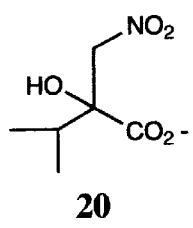
20
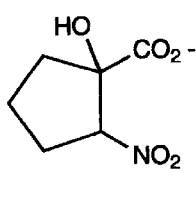
21
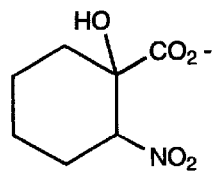
22
Figure 7

METHOD FOR TREATING *MYCOBACTERIUM TUBERCULOSIS*

BACKGROUND OF THE INVENTION

1. Field of the Invention

The present invention is directed to a method for treating tuberculosis in a mammal which comprises administering to the mammal a therapeutically effective amount of an inhibitor compound that inhibits an enzyme in the branched chain amino acid biosynthetic pathway in *Mycobacterium tuberculosis*.

2. Description of the Background

The disclosures referred to herein to illustrate the background of the invention and to provide additional detail with respect to its practice are incorporated herein by reference and, for convenience, are referenced in the following text and respectively grouped in the appended bibliography.

Tuberculosis (TB) kills 2.5 million people annually and the World Health Organization estimated that, at the current rate of increase, there will be 4 million tuberculosis deaths worldwide per year by the year 2005 (Bloom and Murray, 1992). In addition, the percentage of clinical tuberculosis isolates that are resistant to the first-line drugs isoniazid and rifampicin has increased substantially (Collins, 1993; Jacobs, 1994). Outbreaks of drug-resistance tuberculosis have occurred in correctional facilities, hospitals, and urban areas in the United States. Most of the drug-resistant tuberculosis has occurred in patients who are co-infected with HIV and the mortality rate associated with these infections is as high as 90% (Collins, 1993; Dunlap and Kimerling, 1994). The rise in tuberculosis cases in the United States is also attributed to an increase in immigration from areas of the world in which tuberculosis infection rates are high (Dunlap and Kimerling, 1994; Hutchins and Hershfield, 1993). A major part of the strategy to overcome the worldwide tuberculosis problem will be the development of new therapeutic agents to treat this disease (Collins, 1993).

Historically, antimycobacterial drugs were discovered by screening compounds for inhibition of growth of the bacteria. The search for the target site of these compounds occurred after they were shown to be useful antibiotics. For example, isoniazid was introduced as an antimycobacterial drug in 1952 but its target site was not elucidated until 1995 (Dressen et al., 1995). Furthermore, the mechanism of toxicity of isoniazid is still not understood because it is converted by the bacteria to a toxic metabolite that has not been identified (Dressen et al., 1995; Zang and Young, 1993). The target sites of two other first-use drugs, ethambutol (Silve et al., 1993; Takayama and Kilburn, 1989; Wolucka et al., 1994) and pyrazinamide (Heifets et al., 1989) are not yet defined.

Using transposon mutagenesis, McAdam et al. isolated two leucine auxotrophic strains and one methionine auxotrophic strain of *M. bovis* (BCG) (McAdam et al., 1995). Infection of mice with the auxotrophic strains was compared with the parent strain. On day 30 of infection, there were 100-fold more colony-forming units (cfu) of BCG in the spleens and lungs of mice infected with the parent strain than in mice infected with the leucine auxotrophic strains. Conversely, the numbers of colony forming units measured in mice infected with the methionine auxotrophic strain were comparable to the parent strain. Both of the leucine auxotrophic strains contained transposon insertions in the leuD gene, which encodes a subunit of isopropylmalate isomerase (IPMI) (see FIG. 1).

The discovery that the phytotoxic effect of sulfonyl urea herbicides is due to inhibition of the first step in branched chain amino acid synthesis focused a great deal of research on this pathway for development of new herbicides (Hawkes et al., 1989; Schloss, 1994; Schloss et al., 1988). This effort has led to discovery of a large number of branched chain amino acid pathway inhibitors, some of which are produced in large quantity for commercial use.

SUMMARY OF THE INVENTION

The present invention pertains to a method for treating tuberculosis in a mammal which comprises administering to the mammal a therapeutically effective amount of an inhibitor compound that inhibits an enzyme in the branched chain amino acid biosynthetic pathway in *Mycobacterium tuberculosis*.

The present invention also pertains to a therapeutic composition useful for treating tuberculosis in a mammal which comprises an inhibitor compound that inhibits acetolactate synthase and an inhibitor compound that inhibits ketol-acid reductoisomerase in the branched chain amino acid biosynthetic pathway in *Mycobacterium tuberculosis*.

BRIEF DESCRIPTION OF THE FIGURES

FIG. 3 is a diagram showing the structures of the sulfonylurea herbacides having Formula 1. Definitions of the $R_1$ group are given in FIG. 4 and definitions of the $R_2$ and $R_3$ groups are given in FIG. 5.

FIG. 5 is a diagram providing the definitions of the $R_2$ and $R_3$ groups in the structures of the sulfonylurea herbacides having Formula 1, set out in FIG. 3.

FIG. 6 is a diagram showing the structures of the imidazolinones (2–5), the triazolopyrimidine sulfonanilides (6–7, and the pyrimidyloxy salicylic acids (8).

FIG. 7 is a diagram showing (a) a series of N-substituted oxalyl hydroxamates (9–14) synthesized as analogs of the transition state for the rearrangement step of ketol-acid reductoisomerase; (b) O-substituted oxalyl hydroxamates (15–17) as selective inhibitors of isopropylmalate dehydrogenase; (c) an experimental herbicide, the phosphinic acid 2-dimethylphosphinoyl-2-hydroxy acetic acid (18), discovered to be a potent and selective inhibitor of ketol-acid reductoisomerase; (d) the mechanistically related enzyme aconitase, nitronate analogs of the substrates of isopropylmalate isomerase, 19 and 20; and (e) cyclic nitronate analogs, 21 and 22.

DETAILED DESCRIPTION OF THE INVENTION

Figure 1:
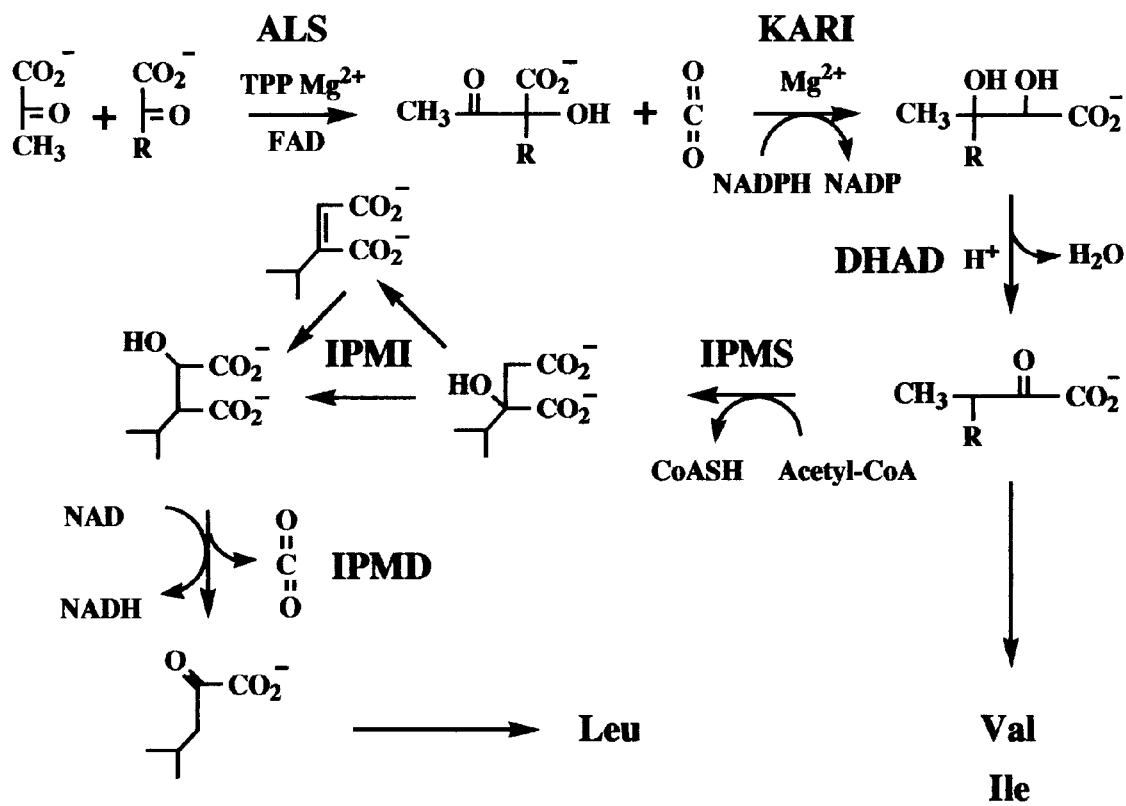
FIG. 1 is a diagram illustrating the pathway for branched chain amino acid biosynthesis. ALS, acetolactate synthase; KARI, ketol-acid reductoisomerase; DHAD, dihydroxyacid, dehydrogenase; IPMS, isopropylmalate synthase; IPMI, isopropylmalate isomerase; IPMD, isopropylmalate dehydrogenase. R=methyl for pyruvate; R=ethyl for α-ketobutyrate.

Applicants have discovered that inhibitors of the branched chain amino acid biosynthetic enzymes of *Mycobacterium*

*tuberculosis*, which supply leucine to the bacteria, would prevent the progress of infection by *Mycobacterium tuberculosis*. Advantages of targeting branched chain amino acid biosynthesis include the following i) new potential drugs may be drawn from the large pool of pre-existing inhibitors currently available in large quantities and used commercially as herbicides; ii) combination therapy with inhibitors of different steps in the pathway offers potential for synergistic inhibition; iii) mammals do not produce the branched chain amino acid biosynthetic enzymes and, therefore, treatment of bacterial infection with compounds that inhibit these enzymes would be specific for the pathogenic organism, decreasing the potential for mammalian toxicity; iv) intensive studies of several bacterial branched chain amino acid biosynthetic enzymes has yielded information that will be very useful in the design of new inhibitors that are specifically selected for inhibition of *Mycobacterium tuberculosis* enzymes.

As set out above, leucine auxotrophic strains of *M. bovis* (BCG) were unable to establish an infection in mice (McAdam et al., 1995). This result suggests that leucine biosynthesis is required for pathogenesis of *Mycobacterium tuberculosis* and that drugs that deprive this organism of the ability to synthesize branched chain amino acids may be effective as antituberculosis agents. Applicants have found that two branched chain amino acid biosynthetic inhibitors are potent inhibitors of *Mycobacterium tuberculosis* growth in vitro and that combining inhibitors of the first and second common steps of the pathway produces highly synergistic growth inhibition. Moreover, applicants have found that sulfometuron methyl, an inhibitor of the first step in the pathway, inhibits growth of *Mycobacterium tuberculosis* in a mouse model system. Compounds that inhibit the branched chain amino acid biosynthetic pathway have therapeutic potential for treating tuberculosis.

The compounds that inhibit the branched chain amino acid biosynthetic pathway in *Mycobacterium tuberculosis* of the present invention can be administered to mammals, e.g., animals or humans, in amounts effective to provide the desired tuberculosis inhibitory activity. Since the activity of the compounds and the degree of the desired therapeutic effect vary, the dosage level of the compound employed will also vary. The actual dosage administered will also be determined by such generally recognized factors as the body weight of the patient and the individual hypersensitiveness of the particular patient. Thus, the unit dosage for a particular patient (man) can vary from as low as about 1 mg per kg of body weight, which the practitioner may titrate to the desired effect. A preferred minimum dose for titration is from about from about 1 mg/kg to about 500 mg/kg body weight, preferably from about 5 mg/kg to about 350 mg/kg body weight, and more preferably from about 10 mg/kg to about 200 mg/kg body weight. A preferred minimum dose for sulfometuron present is about 150 mg/kg body weight.

The present invention is further illustrated by the following examples which are not intended to limit the effective scope of the claims. All parts and percentages in the examples and throughout the specification and claims are by weight of the final composition unless otherwise specified.

EXAMPLES

The following experiments were performed to determine (1) whether inhibitors of the first and second enzymes in the branched chain amino acid biosynthetic pathway inhibit growth of *Mycobacterium tuberculosis* in vitro; (2) the minimum inhibitory concentration (MIC) of these inhibitors; and 3) whether injections of an inhibitor of branched chain amino acid biosynthesis prevent growth of *Mycobacterium tuberculosis* in vivo in a mouse model system.

*Mycobacterium tuberculosis* Strains Used in These Studies.

Strain RC1 is a clinical isolate obtained from a patient sample that was submitted to the Kennedy Memorial Hospitals Microbiology Laboratory, Cherry Hill, N.J. Strain ATCC35801 was from the American Type Culture Collection and was selected for this study because it was virulent in mice (Klemens et al., 1994).

*Mycobacterium tuberculosis* Growth in vitro was Prevented by Acetolactate Synthase (ALS) Inhibitors Sulfometuron methyl (SM) is a herbicidal compound that inhibits acetolactate synthase, the first common enzyme in the branched chain amino acid biosynthetic pathway (FIG. 1) (Schloss et al., 1988). The minimum inhibitory concentration for growth of *Mycobacterium tuberculosis* was determined by an agar dilution method (described below) using medium containing no branched chain amino acids or medium supplemented with branched chain amino acids. The clinical isolate, strain RC1, was more sensitive to inhibition by sulfometuron methyl (minimum inhibitory concentration=0.3 µg/ml) than was strain ATCC35801 (minimum inhibitory concentration=3.6 µg/ml) (Table 1). These minimum inhibitory concentrations were in the same range as first-line antituberculosis drugs, which ranged from 0.2 µg/ml for isoniazid to 16 µg/ml for pyrazinamide (Table 2). Addition of isoleucine and valine to the plates did not prevent inhibition of strain RC1 by sulfometuron methyl (not shown). Addition of leucine, isoleucine, and valine (LIV) to the medium, however, partially reduced the toxicity of sulfometuron methyl towards strain RC1 (minimum inhibitory concentration=1.8 µg/ml). Leucine, isoleucine, and valine addition also prevented the toxicity of sulfometuron methyl towards strain ATCC35801 (minimum inhibitory concentration >3.6 µg/ml). Chlorsulfuron, another sulfonylurea herbicide that inhibits acetolactate synthase, inhibited the growth of *Mycobacterium tuberculosis* strain RC1 (minimum inhibitory concentration=4.4 µg/ml. Addition of leucine, isoleucine, and valine to the growth medium completely reversed the effects of chlorsulfuron (minimum inhibitory concentration >35 µg/ml). Typically, medium used for minimum inhibitory concentration determinations with mycobacteria contains bovine serum albumin (BSA) or sodium oleate and bovine serum albumin, which stimulate growth of mycobacteria. When the medium was supplemented with bovine serum albumin or with sodium oleate and bovine serum albumin, the minimum inhibitory concentrations for sulfometuron methyl against strain RC1 were significantly increased (minimum inhibitory concentrations=4.4 µg/ml and 2.2 µg/ml, respectively) suggesting that the bovine serum albumin preparation used in these experiments contained free leucine, isoleucine, and valine (not shown).

Susceptibility of *Mycobacterium tuberculosis* to Ketol-acid Reductoisomerase Inhibitors in vitro.

Ketol-acid reductoisomerase (KARI) catalyzes the second common step in branched chain amino acid biosynthesis (see FIG. 1). N-Isopropyloxayl hydroxamate (IpOHA) and 2-dimethylphosphinoyl-2-hydroxy acetic acid (Hoe 704) are transition state analogs that bind to the active site of ketol-acid reductoisomerase (Aulabaugh and Schloss, 1990; Schloss and Aulabaugh, 1990; Schulz et al., 1988) and are potent inhibitors of this enzyme. N-isopropyloxayl hydroxamate and 2-dimethylphosphinoyl-2-hydroxy acetic acid were tested for antimycobacterial activity by the agar dilution method (Table 1). N-isopropyloxayl hydroxamate was slightly more effective against strain RC1 (minimum inhibitory concentration=9.2 µg/ml) than it was against strain ATCC35801 (minimum inhibitory concentration=18 µg/ml). Addition of branched chain amino acids did not reverse the toxic effects of N-isopropyloxayl hydroxamate on strain RC1. In contrast, branched chain amino acids decreased the toxicity of N-isopropyloxayl hydroxamate against strain ATCC35801 (minimum inhibitory concentration>18 µg/ml). 2-dimethylphosphinoyl-2-hydroxy acetic acid was not inhibitory to growth of strain RC1 at concentrations up to 37 µg/ml and was not tested against strain ATCC35801

Synergistic Inhibition by Sulfometuron Methyl and N-isopropyloxayl Hydroxamate

Since sulfometuron methyl and N-isopropyloxayl hydroxamate inhibit two separate steps in the branched chain amino acid pathway, a mixture of these compounds was tested for synergistic growth inhibition. Medium containing 3.6 µg/ml sulfometuron methyl and 18 µg/ml N-isopropyloxayl hydroxamate was prepared and concentrations were varied by serial 2-fold dilutions. Although strain ATCC35801 grew well on plates containing no inhibitor, it did not grow on any of the plates containing the combination of sulfometuron methyl and N-isopropyloxayl hydroxamate. The results indicated a greater than 250-fold synergy between the two inhibitors (minimum inhibitory concentration<0.01 µg/ml sulfometuron methyl; <0.07 N-isopropyloxayl hydroxamate) as compared to either sulfometuron methyl alone (minimum inhibitory concentration=3.6 µg/ml) or N-isopropyloxayl hydroxamate alone (minimum inhibitory concentration=18 µg/ml) (Table 1). Addition of leucine, isoleucine, and valine to plates containing the combination of sulfometuron methyl and N-isopropyloxayl hydroxamate completely alleviated the effects of these compounds (minimum inhibitory concentration>3.6 µg/ml sulfometuron methyl; >18 µg/ml N-isopropyloxayl hydroxamate), indicating that the toxic effect was due to inhibition of branched chain amino acid biosynthesis (Table 1).

Sulfometuron Methyl was Effective at Inhibiting the Progress of Tuberculosis Infection.

Figure 2:
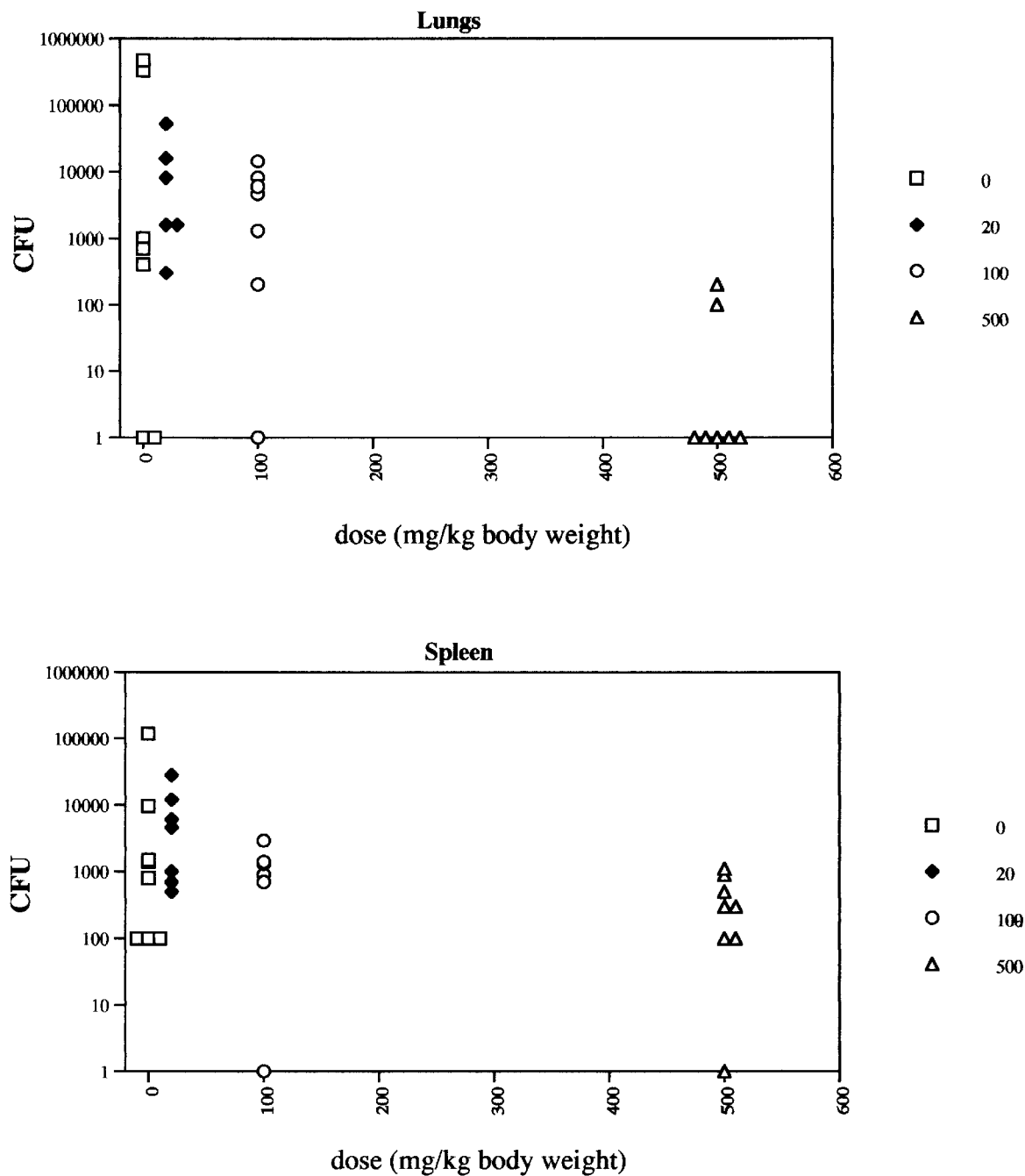
FIG. 2 illustrates the effect of sulfometuron methyl (SM) injections on *Mycobacterium tuberculosis* growth in lungs and spleens of infected mice. Treatment was initiated on day 5 of infection and was administered each day for 31 days. Mice were then sacrificed for determination of *Mycobacterium tuberculosis* colony forming units (cfu). Symbols: squares, phosphate bufferd saline; diamonds, 20 mg sulfometuron methyl/kg body weight; circles, 100 mg sulfometuron methyl/kg body weight; triangles, 500 mg sulfometuron methyl/kg body weight.
Figure 4:
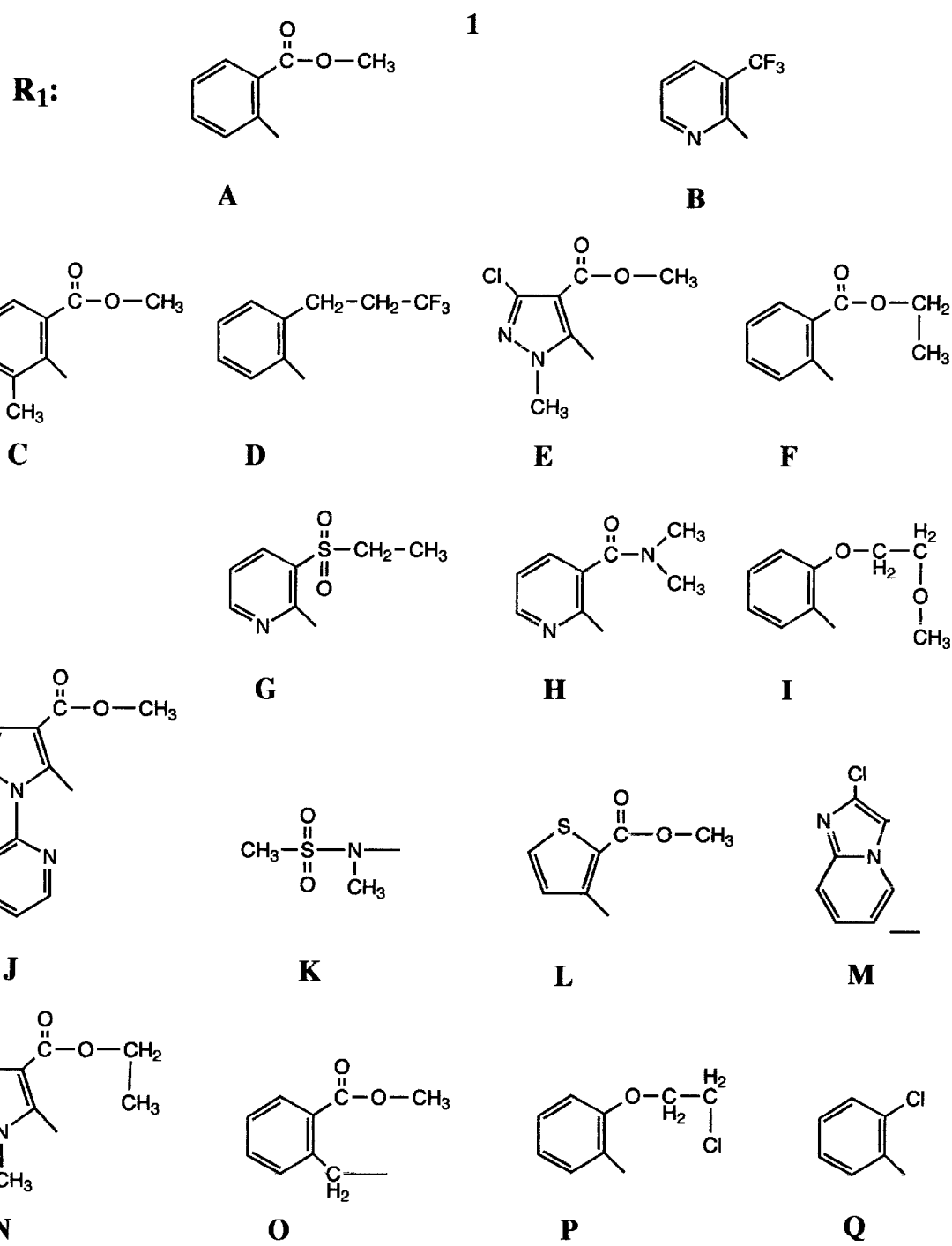
FIG. 4 is a diagram providing the definitions of the $R_1$ group in the structures of the sulfonylurea herbacides having Formula 1, set out in FIG. 3.

Mice were infected with *Mycobacterium tuberculosis* strain ATCC35801 and injections of either sulfometuron methyl or phosphate buffered saline (PBS) were administered each day for 31 days beginning 5 days post-infection. Infection was measured by homogenizing spleens and lungs and plating homogenates to determine colony forming units (cfu) of *Mycobacterium tuberculosis*. The most striking result from the mouse study was the lower colony forming units in the lungs of the mice given 500 mg sulfometuron methyl /kg body weight as compared to the other groups (FIG. 2). Thirteen out of 20 (65%) mice in groups that received either phosphate buffered saline, 20 mg sulfometuron methyl/kg, or 100 mg sulfometuron methyl/kg had more than $10^3$ colony forming units in the lungs, whereas none of the eight mice in the group that received 500 mg sulfometuron methyl/kg had more than 200 colony forming units in the lungs (FIG. 2). Because of the small number of samples and the heterogeneity of the variance across the four groups, we used a non-parametric Kruskal-Wallis statistical analysis to determine if there were differences between the values obtained for the four groups of mice (Siegel, 1956). The results of this analysis suggested that there was an overall difference between the values obtained from the lungs of the four groups (Table 3). The Mann-Whitney U test was used to determine which groups differed from each other (Siegel, 1956). This test showed that there was a significant difference between groups that received phosphate buffered saline, 20 mg sulfometuron methyl/kg, and 100 mg sulfometuron methyl/kg when each was compared individually with the group that received 500 mg sulfometuron methyl/kg (Table 4). We concluded from this that sulfometuron methyl given at a dose 500 mg/kg body weight significantly reduced growth of *Mycobacterium tuberculosis* in the lungs.

The data from the spleen samples also suggested that sulfometuron methyl inhibited infection in this organ but statistical analysis did not support this conclusion. About half of the mice in groups that received either phosphate buffered saline, 20 mg sulfometuron methyl/kg, or 100 mg sulfometuron methyl/kg (12/23=52%) had over $10^3$ colony forming units/spleen whereas only 1 of 8 mice (13%) in the group that received 500 mg sulfometuron methyl/kg had more than $10^3$ colony forming units /spleen. The Kruskal-Wallis analysis indicated that there were no statistically significant differences in the values obtained from the spleen samples (P>0.05), preventing us from concluding with confidence that sulfometuron methyl inhibited growth of *Mycobacterium tuberculosis* in the spleen.

Methods

Determination of Minimum Inhibitory Concentration

Minimum inhibitory concentrations were determined by an agar dilution method (Murray, 1995). Minimal medium was Middlebrook 7H10 agar medium base (Gibco) supplemented 0.5% glycerol, 0.2% glucose, and 34 mM NaCl. This medium contained no amino acids. In some experiments the 7H10 agar was supplemented with 5 g/L bovine serum albumin fraction V (7H10 ADC), or with 5 g/l, bovine serum albumin fraction V and 50 mg/L sodium oleate (7H10 OADC). Serial two-fold dilutions of concentrated stock compound were prepared and added to the molten agar at 50° C. prior to pouring it onto petri plates. To prepare medium containing isoleucine and valine or leucine, isoleucine, and valine (LIV), stock solutions of the amino acids were added to the molten agar to give final concentrations of 35 mg/L isoleucine, 70 mg/L valine, and 70 mg/L leucine. To inoculate agar medium, frozen stock cultures of *Mycobacterium tuberculosis* (stored at –80° C.) were used to prepare slant cultures on Middlebrook 7H11 medium (Becton-Dickenson) containing casein hydrolysate, bovine serum albumin, and sodium oleate. The slant cultures were incubated for 3 weeks at 37° C. in a 10% $CO_2$ atmosphere. Slant cultures were used to inoculate Middlebrook 7H10 agar minimal medium, the plates were incubated for 3 weeks at 37° C., and cells from the plates were suspended in liquid Middlebrook 7H9 minimal medium by vortexing extensively in the presence of glass beads (Middlebrook 7H9 is the same as 7H10 except that 7H9 contains no agar). The suspension was allowed to settle for 10 minutes and was diluted to a density that matched a McFarland #1 standard. Fifty µl of suspension was used to inoculate plates, the liquid was allowed to dry, and the plates were incubated at 37° C. in a 10% $CO_2$ atmosphere for 3–4 weeks. The minimum inhibitory concentration was defined as the lowest concentration of the compound that prevented growth of the organism.

Mouse Studies

To determine if high doses of sulfometuron methyl would be toxic to mice, a 20 mg/ml solution of this compound was prepared in phosphate buffered saline and 0.5 ml of this was injected subcutaneously into 4 day-old CD-1 female mice each day for 30 days. This dose corresponded to 500 mg sulfometuron methyl/kg body weight of the mouse. After the 30-day course of treatment the mice were sacrificed and the internal organs were examined by a veterinarian trained in laboratory animal care. The organs were compared to a control group that received injections of phosphate buffered saline. No significant differences were seen in either the behavior of the mice or the condition of the internal organs when the sulfometuron methyl-injected mice were compared to the phosphate buffered saline-injected mice.

For the tuberculosis mouse model study, a modification of the method of Klemens et al. (Klemens et al., 1994) was used. Slant cultures of *Mycobacterium tuberculosis* strain ATCC35801 were prepared by inoculation of Middlebrook 7H 11 with a frozen glycerol stock culture. The slants were grown for 3 weeks at 37° C. in a 10% $CO_2$ atmosphere. These cultures were subcultured onto another Middlebrook 7H11 slant and a cell suspension was prepared in Middlebrook 7H9 medium. The suspension was vortexed rigorously with glass beads in the tube to disrupt clumps of bacteria and was allowed to settle for 10 minutes prior to adjusting the cell density to match a 0.5 McFarland standard (approximately $1.5 \times 10^8$ cells/ml). A quantity of $10^7$ cells was injected into the tail vein of each mouse in a volume of 0.2 ml. Beginning five days after injection of *Mycobacterium tuberculosis*, subcutaneous injections of 0.5 ml phosphate buffered saline or 0.5 ml sulfometuron methyl solution were given each day for 31 days. There were 4 groups of 8 mice. Phosphate buffered saline was given to one group and the remaining 3 groups received sulfometuron methyl doses of 20 mg/kg body weight, 100 mg/kg body weight, or 500 mg/kg body weight. Mice were sacrificed during a 3 day period immediately following the last injection. Spleens and lungs were removed and homogenized in 1 ml of phosphate buffered saline using a Dounce homogenizer. The homogenates were diluted in phosphate buffered saline and plated on Middlebrook 7H10 OADC medium. Plates were incubated at 37° C. in a 10% $CO_2$ atmosphere for 4 weeks and colonies (colony forming units) were counted.

Synthesis and Evaluation of Inhibitors of Branched Chain Amino Acid Biosynthesis There are three enzymes common to the biosynthesis of all three branched chain amino acids, leucine, isoleucine, and valine. They are acetolactate synthase (ALS), ketol-acid reductoisomerase (KARI), and dihydroxy acid dehydratase (DHAD) (FIG. 1). There are three enzymes unique to leucine biosynthesis; these are isopropylmalate synthase (IPMS), isopropylmalate isomerase (IPMI), and isopropylmalate dehydrogenase (IPMD). Not included in this discussion are the transaminases, for which corresponding enzymes would exist in humans, or the enzymes linking isoleucine (aspartate family) to aspartate through threonine, since it is not presently known whether pathogenic mycobacteria can obtain threonine from an infected host organism. Of the remaining six branched chain amino acid biosynthetic enzymes, there are potent inhibitors known for five that may have potential as antimycobacterial drugs. Inhibitors for four of these enzymes, acetolactate synthase, ketol-acid reductoisomerase, isopropylmalate isomerase, and isopropylmalate dehyrogenase, will be discussed in detail as within the scope of the present invention. Although inhibitors are known for the fifth enzyme, dihydroxy acid dehydratase, the inhibitors will not be discussed in detail because of their more modest potency, relative to the inhibitors for other enzymes, a lack of clear potential for development of greater potency, and that a high degree of selectivity for the target enzyme in vivo for one or more organisms has not been established (Flint and Nudelman, 1993; Pirrung et al., 1989). These criteria have been met by the known inhibitors of the other four enzymes (Hawkes et al., 1993; Wittenbach et al., 1992). Further, inhibition of acetolactate synthase, ketol-acid reductoisomerase, isopropylmalate isomerase, and isopropylmalate dehyrogenase in plants is cidal, although the underlying toxicology by which inhibition of these enzymes causes death remains unclear (Schloss, 1994; Wittenbach et al., 1992). Although inhibition of the corresponding enzymes in enteric bacteria (primarily *Escherichia coli* and *Salmonella typhimurium*) appears to be static, rather than cidal, the long term effect of any of these inhibitors, alone or in combination, on any microorganism has yet to be carefully examined. Further, since the slow rate of growth of pathogenic mycobacteria is much closer to that of plants than those microorganisms that have been examined to date, there is some reason to hope that their physiological response to inhibition of these enzymes may be similar (i.e. cidal).

Acetolactate Synthase. Of the inhibitors of branched chain amino acid biosynthesis, only inhibitors of acetolactate synthase have been commercialized as herbicides. There are literally thousands of structurally diverse inhibitors known for this enzyme (Schloss et al., 1988). The mechanism of action of these inhibitors is rather unusual, in that they appear to bind to an evolutionary vestige of a quinone cofactor site, that is no longer functional in acetolactate synthase. The inhibitors capture a form of the enzyme that is prone to oxidative inactivation, such that over a short period of time they are reversible yet time dependent, but eventually they can induce irreversible inactivation (Schloss, 1994). Since these inhibitors are not really active site directed nor interact with essential structural features of acetolactate synthase, resistant forms of the enzyme can readily be obtained that are uncompromised in catalytic function (Falco et al., 1985). Although active site directed inhibitors of acetolactate syntliase are known (Abell et al., 1995), they are far less potent than the other inhibitors and have little potential for biologic activity. Despite the possibility of resistance, the commercialized inhibitors of acetolactate synthase have proven to be extremely effective herbicides. Selection for resistance by crop vs. weed species has been achieved by obtaining selective metabolism of inhibitors in the crop plant, rather than resistance at the enzyme level (Brown and Cotterman, 1994).

There are approximately 28 different inhibitors of acetolactate synthase that have been or are soon to be commercialized as herbicides (structures 1 through 8, FIGS. 3–6). These structures fall into four different classes of chemistry, the sulfonylureas (1, 21 examples given, FIGS. 3–5), the imidazolinones (2–5, FIG. 6), the triazolopyrimidine sulfonanilides (6–7, FIG. 6), and the pyrimidyloxy salicylic acids (8, FIG. 6). Once these structures are in use as components of weed control formulations, the reagent grade chemicals are commercially available from ChemService, West Chester, Pa. The sulfonylureas (1) are the most structurally diverse set of acetolactate synthase inhibitors. For the commercial structures there have been 17 different substituents utilized at the $R_1$ position, 8 different pyrimidines or triazines utilized at the $R_2$ position, and one compound in which the hydrogen normally present at the $R_3$ position was replaced with a methyl. The chemistry of these different substituents ($R_1$ and $R_2$) has recently been reviewed (Gee and Hay, 1994) and the synthesis of these and other various substituents is well documented. The general synthetic method for the sulfonylureas lends itself readily to a combinatorial approach. As illustrated, condensation of a sulfonyl isocyanate with a primary or secondary amine readily gives 1 in good yields. The sulfonyl isocyanate can be prepared by reaction of the sulfonyl chloride with sodium cyanate (Gee and Hay, 1994).

Combinatorial Synthesis of Sulfonylureas

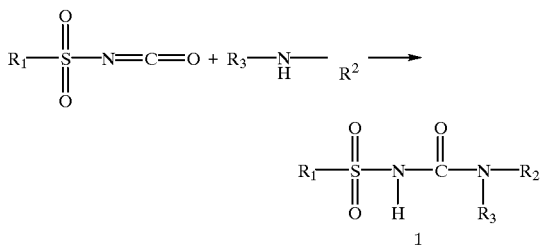

This method of synthesis would allow for the facile preparation of isotopically labeled sulfonylureas (from $^{14}$C-cyanate) for metabolic or distribution studies in vivo. Alternatively, a sulfonylamide (R$_1$) can be condensed with a heterocyclic structure (R$_2$) containing an isocyanate substituent (Gee and Hay, 1994). Restricting a combinatorial approach to those R$_1$, R$_2$, and R$_3$ substituents of 1 that have been utilized in commercialized sulfonylureas would give 272 different structures, only 21 of which have been developed as commercial herbicides.

Synthesis for combinatorial optimization of inhibitory sulfonylureas can be carried out by multiplex syntheses (multiple simultaneous syntheses) (Mitscher, 1995) such as with a combinatorial reactor. The reactor consists of a benchtop orbit shaker (Lab-Line), a DIGI-BLOCK heater (Aldrich) with three DIGI-BLOCK heating blocks, capable of holding 24 or 12 tubes each. Thus, 72 tubes with dimensions of 13×100 mm, or 36 tubes (25×50 mm) are available as reaction vessels. With this reactor, reactions can be carried out at room temperature, at elevated temperature and under an inert gas atmosphere. The reaction vessel can also be equipped with a reflux condenser made from a Wheaton chromatography column, filled with 3 mm glass beads. For anhydrous conditions the tubes are fitted with rubber caps into which syringe needles, connected to argon, are placed. Since the multiplex apparatus has a maximum of 72 reaction vessels, 72 reactions can be carried out simultaneously. Syringes, attached to commercially available Waters-Vacuum Manifold can be used to filter 24 samples at once. This set-up is also of utility for column chromatography (easy separations only) or can be put to use for solvent separations (separatory funnel). The multiplex reactor and the Waters-Vacuum Manifold apparatus have been used successfully in the Mitscher group to prepare libraries of hundreds of novel quinolone antibacterial agents and other drug candidates by muliplex syntheses. While use of such equipment is not essential, it will be helpful, and adapting the work to this format would make an extension of the project beyond the 272 target structures easier.

Evaluation of the commercially available inhibitors of acetolactate synthase (1–8) and the sulfonylureas prepared by combinatorial synthesis can be carried out by use of a fixed-time, colorimetric assay for the enzyme (Tse and Schloss, 1993). The assay can easily be used to measure activity from crude extracts of plants or bacteria. Assays have been successfully adapted to a microtitre plate format, compatible with running 96 single-time-point measurements simultaneously. Extracts (Allaudeen and Ramakrishnan, 1971; Allaudeen and Ramakrishnan, 1970; Allaudeen and Ramakrishnan, 1968) from γ-irradiated *Mycobacterium tuberculosis* H$_{37}$Rv (70 g of this organism have been obtained from Prof. John Belisle, Tuberculosis Research Materials, prepared under NIAID contract number N01 AI25147, and grown on Proskaur Beck minimal media to maximize expression of the enzymes specific to branched chain amino acid biosynthesis) can be assayed concurrently with purified acetolactate synthase isozyme I from *E. coli* and isozyme II from *S. typhimurium* as positive controls and for comparative purposes (Aulabaugh and Schloss, 1990; Schloss and Van Dyk, 1988).

Ketol-acid Reductoisomerase. A series of N-substituted oxalyl hydroxamates (9–14) were synthesized as analogs of the transition state for the rearrangement step of ketol-acid reductoisomerase (FIG. 7) (Aulabaugh and Schloss, 1990). At all concentrations tested these compounds are virtually irreversible inhibitors of the *E. coli* (bacterial) and *Arabidopsis thaliana* (plant) ketol-acid reductoisomerase (Aulabaugh and Schloss, 1988). Determination of the potency of these compounds required the synthesis of $^{14}C$-labeled N-isopropyloxayl hydroxamate (12). In the presence of $Mg^{2+}$ and NADPH, [$^{14}C$]N-isopropyloxayl hydroxamate forms a nearly irreversible complex with the *E. coli* ketol-acid reductoisomerase. Half of the ketol-acid reductoisomerase-bound N-isopropyloxayl hydroxamate will exchange with unbound N-isopropyloxayl hydroxamate in six days (overall dissociation constant=20 pM). Increasing the substituent on nitrogen from a hydrogen (9) to a benzyl group (13) increased the association rate for the inhibitor modestly (Aulabaugh and Schloss, 1990). Further increasing the size of the substituent to a 12-carbon chain (14) gave an inhibitor comparable in potency to 13 (Aulabaugh & Schloss, unpublished), indicating that the substituent on nitrogen was directed out of the enzyme active site. These results would suggest that the substituent on nitrogen can be varied to optimize transport and detoxification properties of the inhibitor without compromising intrinsic activity against the enzyme. Compounds 10–12 are lethal to several plant species as well as being potent inhibitors of the growth of *E. coli* on minimal media (Aulabaugh and Schloss, 1990; Schloss and Aulabaugh, 1990; Wittenbach et al., 1991). Addition of branched chain amino acids to the growth media will protect both plants and bacteria against the effects of the oxalyl hydroxamates, indicating that these are highly selective inhibitors for this biosynthetic pathway. High concentrations of N-isopropyloxayl hydroxamate (1 mM) has no effect on the other two common enzymes of branched chain amino acid biosynthesis from *E. coli*, acetolactate synthase or dihydroxy acid dehydratase.

An experimental herbicide, the phosphinic acid 2-dimethylphosphinoyl-2-hydroxy acetic acid (18, FIG. 7), was also discovered to be a potent and selective inhibitor of ketol-acid reductoisomerase from carrot (plant) (Hawkes and Edwards, 1990; Schulz et al., 1988), *E. coli* (Aulabaugh and Schloss, 1988; Schulz et al., 1988) and *Klebsiella pneumoniae* (Schulz and Taggeselle, 1990). Although 2-dimethylphosphinoyl-2-hydroxy acetic acid does not inhibit the growth of *E. coli* (Aulabaugh and Schloss, 1990), it does inhibit the growth of *K. pneumoniae* (Schulz and Taggeselle, 1990). Interestingly, reversal of the growth inhibitory effect of 2-dimethylphosphinoyl-2-hydroxy acetic acid on *K. pneumoniae* requires both branched chain amino acids and pantoate or (Schulz and Taggeselle, 1990), unlike the effect on carrot cells in culture that can be reversed by branched chain amino acids alone (Schulz et al., 1988). The inhibitory effect of 2-dimethylphosphinoyl-2-hydroxy acetic acid on *K. pneumoniae* is still due to potent and selective inhibition of ketol-acid reductoisomerase and suggests that in this organism ketol-acid reductoisomerase plays a significant role in pantoate biosynthesis (Schulz and Taggeselle, 1990).

The oxalyl hydroxamates (9–14) can readily be synthesized from methyl oxalyl chloride and the appropriate N-substituted hydroxylamine (Aulabaugh and Schloss, 1990; Aulabaugh and Schloss, 1988). If the N-substituted hydroxylamine is not commercially available (11, 14), it can be conveniently synthesized by reducing the imine formed from the aldehyde and hydroxylamine with sodium cyanoborohydride (Aulabaugh and Schloss, 1990; Aulabaugh and Schloss, 1988). The methyl esters of the oxalyl hydroxamates seem to be only several-fold less potent as inhibitors of the *E. coli* (bacteria) or *Arabidopsis thaliana* (plant) enzymes in vitro, than the corresponding potassium salts of their free carboxylates (Aulabaugh and Schloss, 1988). Similarly, the methyl esters and potassium salts of 10–12 have similar effects on the growth of *E. coli* and *A. thaliana* on minimal media (Aulabaugh and Schloss, 1988). The rates of hydrolysis of the esters appear to be far too slow to account for the former observation by hydrolysis of these esters under assay conditions (Aulabaugh & Schloss, unpublished observation). In any case, both the esters and salts of these compounds can be tested as inhibitors of mycobacterial growth and as inhibitors of the enzyme in vitro.

It has been reported that mycobacteria have both ketol-acid reductoisomerase and an ascorbate-dependent enzyme that catalyzes the isomerization of a β-keto acid to an α-keto acid (Allaudeen and Ramakrishnan, 1971; Allaudeen and Raniakrishnan, 1970; Allaudeen and Ramakrishnan, 1968). Since the equilibrium of this isomerization lies far in the non-physiological, β-keto acid direction (Aulabaugh and Schloss, 1990), the physiological relevance of the latter enzyme to branched chain amino acid biosynthesis seems dubious. However, to avoid missing such an activity, crude extracts from mycobacteria can be used to evaluate inhibitors by use of two different assays. In the first assay, the α-keto acid (2-oxo-3-hydroxy-3-methylbutyrate) can be allowed to isomerize to the β-keto acid (acetolactate) in the presence of NADP and $Mg^{2+}$. The *E. coli* enzyme will also catalyze this isomerization (Aulabaugh and Schloss, 1990). Incubations can be quenched with acid and worked up by the same protocol used in the fixed-time assay for acetolactate synthase (Tse and Schloss, 1993). This assay will rely on the formation of acetoin by acid-catalyzed decarboxylation of acetolactate (the β-keto acid). Such an assay should be compatible with measuring activity in crude extracts of plants or bacteria. Purified *E. coli* ketol-acid reductoisomerase (already available in Prof. Schloss' laboratory) can be used as a positive control and for comparative purposes. A second assay will also be employed, that utilizes [$^{14}$C-carboxy]acetolactate. The radiolabeled acetolactate can be prepared from commercially available [1-$^{14}$C]pyruvate and purified acetolactate synthase isozyme II (also available in Prof. Schloss' laboratory). Conversion of [$^{14}$C]acetolactate to 2,3-dihydroxy-3-methyl[1-$^{14}$C]butyrate by the action of ketol-acid reductoisomerase and NADPH results in the conversion of the acid labile radioactivity (α, β-keto acid) to an acid stable form (an α,β-dihydroxy acid). This radiometric assay has been used successfully to evaluate inhibitors of ketol-acid reductoisomerase in crude extracts from bacteria and plants (Aulabaugh and Schloss, 1988). Both assays will also be conducted in the presence of ascorbate, but in the absence of NADPH, to test for the presence of the ascorbate-dependent isomerase reported by Allaudeen & Ramakrishnan (Allaudeen and Ramakrishnan, 1970; Allaudeen and Ramakrishnan, 1968).

Isopropylmalate Isomerase. Similar to the mechanistically related enzyme aconitase, nitronate analogs of the substrates of isopropylmalate isomerase, 19 and 20 (FIG. 7), are potent inhibitors of the yeast enzyme, presumably by virtue of their structural similarity to carbanionic reaction intermediates (Emptage, 1990; Emptage and Schloss, 1986). These compounds have no affect on the growth of yeast on minimal media, however, most likely due to the rapid rate at which these compounds decompose (retro-aldol) in the presence of divalent metals (Schloss, unpublished observation). The problem of stability was overcome by use of cyclic nitronate analogs, 21 and 22 (Hawkes et al., 1993). An additional consideration is the affect that the ring has on the nitro alkane's $pK_A$, since only the nitronate forms of these compounds are good inhibitors of isopropylmalate isomerase (Emptage, 1990; Emptage and Schloss, 1986; Hawkes et al., 1993). In contrast to compounds 19 and 22, that have $pK_A$s for ionization of the nitro alkane of 9.5 and 11.1, respectively, the $pK_A$ for 21 is 7.3 (Hawkes et al., 1993). Thus, the cyclopentane ring of 21 insures stability of the molecule, while at the same time lowering the $pK_A$ of the carbon acid. Although in their fully ionized, nitronate forms, 19 and 21 are comparable as inhibitors of the yeast isopropylmalate isomerase, under physiological conditions (pH 7) 21 is a much more potent inhibitor than 19. The herbicidal activity of 21 is also reversed by leucine alone (Hawkes et al., 1993). Synthesis of 21 can be carried out as described (Burrows and Turner, 1966; Hawkes et al., 1993) and evaluated by use of β-isopropylmalate (Schloss et al., 1988) and crude mycobacterial extracts. Since the enzyme from yeast is known to be an iron-sulfur protein and exceedingly labile (Emptage, 1990), it may prove to be rather difficult to evaluate the intrinsic activity of 21 for the mycobacterial isopropylmalate isomerase. An alternate assay, that may prove to be more sensitive and compatible with crude extracts, would be to use dimethylcitraconate as substrate (Schloss et al., 1988) and add purified *S. typhimurium* isopropylmalate dehyrogenase, NAD, and $Mg^{2+}$ to convert the β-isopropylmalate to 2-oxo-4-methylpentanoate and $CO_2$. The resultant 2-oxo-acid can be assayed colorimetrically with dinitrophenylhydrazine (Wittenbach et al., 1994).

Isopropylmalate Dehyrogenase. Based on the observation that the herbicidal effect of the O-substituted oxalyl hydroxamates in plants (pea root cultures) could be reversed by leucine alone, it was discovered that the O-substituted oxalyl hydroxamates (15–17) are selective inhibitors of isopropylmalate dehyrogenase (Wittenbach et al., 1992; Wittenbach et al., 1994) (FIG. 7). Compared to isopropylmalate dehyrogenase, the O-substituted oxalyl hydroxamates (15–17) are rather poor inhibitors of ketol-acid reductoisomerase (Aulabaugh and Schloss, 1988; Wittenbach et al., 1992; Wittenbach et al., 1994). Compounds 15–17 are potent inhibitors of the purified *S. typhimurium* and crude pea isopropylmalate dehyrogenase (Wittenbach et al., 1992; Wittenbach et al., 1994). These compounds do not inhibit either of the other two enzymes specific to leucine biosynthesis, isopropylmalate synthase or isopropylmalate isomerase (Wittenbach et al., 1992). Synthesis of 15–17 can be conducted as previously described (Aulabaugh and Schloss, 1988; Wittenbach et al., 1994) and these compounds can be evaluated as inhibitors of isopropylmalate dehyrogenase from crude extracts of mycobacteria by use of the fixed-time, colorimetric assay that employs dintrophenylhydrazine (Wittenbach et al., 1994). Recently, analogs of 15–17 have been reported, but the potency of these compounds is rather modest, their in vivo selectivity has yet to be established, and they do not merit further consideration at this time (Pirrung et al., 1994).

Susceptibility of *Mycobacterium tuberculosis* to Branched Chain Amino Acid Biosynthetic Pathway Inhibitors in vitro.

*Mycobacterium tuberculosis* strain ATCC35801 can be used to measure minimum inhibitory concentrations because it is the strain that can be used for the mouse model studies. To accommodate the large number of inhibitors to be tested, the agar dilution assay can be modified so that it can be performed in 24-well covered microtiter dishes. With this modification, several inhibitors can be tested simultaneously. Initial pilot screening can be done with medium containing high concentration of inhibitor to identify those compounds that inhibit *Mycobacterium tuberculosis* growth. Any compound that inhibits growth at high concentration can be tested further by performing serial dilutions to determine the minimum inhibitory concentration. The methods can be validated by determining minimum inhibitory concentrations for rifampicin and isoniazid.

Compounds that are determined to have a low minimum inhibitory concentration (<50 mg/ml) can be tested for bactericidal activity using a tube dilution assay. A plate of Middlebrook 7H10 minimal medium can be inoculated from a 7H11 slant culture and incubated for 3 weeks at 37° C. Cells from the plate can be used to inoculate 100 ml of Middlebrook 7H9 minimal medium supplemented 0.05 % Tween 80 in a Cytostir flask (Kontes). The liquid culture can be incubated at 37° C. with constant stirring until the density is approximately $10^8$ cells/ml as determined by absorbance. The culture can be diluted to $10^6$ cells/ml, and divided into 5 ml aliquots to which various concentrations of the inhibitor can be added. The starting colony forming units in these cultures can be determined by removing a sample, sonicating briefly to disrupt clumps of bacteria, and plating for colony counts. The cultures can be incubated for 20 days, samples can be removed, and final colony forming units can be determined. If the inhibitor is bactericidal, then the final colony forming units measured in cultures containing inhibitor will be lower than the starting colony forming units in the same culture. The minimum concentration of inhibitor that causes a significant decrease in colony forming units can be defined as the minimum bactericidal concentration (MBC).

Methods for minimum inhibitory concentration and minimum bactericidal concentration determination using 24-well microtiter plates can be developed. Microtiter plate cultures containing liquid minimal medium with various concentrations of inhibitor can be inoculated with exponentially growing *Mycobacterium tuberculosis*. Starting colony forming units can be measured, cultures can be incubated with slow aeration at 37° C., and growth can be monitored both visually and by a colormetric method using Alamar blue (Yajko et al., 1995). Alamar blue (Sensitire/Alamar, Westlake, Ohio) is an indicator that changes from blue to pink in the presence of growing *Mycobacterium tuberculosis*. Indicator can be added to the wells and cultures will heated to 50° C. for 2 hours to allow color to develop. If the culture contains growing mycobacteria, the indicator turns blue. To determine the incubation time required to produce detectable growth, duplicate cultures can be incubated at 37° C. for 7, 10, and 14 days and the colorimetric test can be performed. When the incubation time required for calorimetric detection has been established, this incubation time can be used for measurements of minimum inhibitory concentrations. Because the color development with the Alamar blue assay involves a 50° C. incubation and will probably affect viability of the bacteria, determination of minimum bactericidal concentration can be performed with a separate set of cultures. Once the minimum inhibitory concentration has been established, minimum bactericidal concentration can be determined by removing samples from cultures containing inhibitor and comparing starting and final colony forming units as described above. For controls, the minimum bactericidal concentration and minimum inhibitory concentration of rifampicin and isoniazid can be determined.

Measurement of Synergy Between Antimycobacterial Compounds

Compounds that inhibit different steps of branched chain amino acid synthesis may be synergistic with respect to growth inhibition. This was demonstrated when a combination of sulfometuron methyl and N-isopropyloxayl hydroxamate, inhibitors for the first and second steps in the branched chain pathway, respectively produced a 250-fold decrease in minimum inhibitory concentration (Table 1). Inhibitors that show a significantly low minimum inhibitory concentration (<50 μg/ml) can be combined with inhibitors of different steps in the pathway to determine if there is synergy between these compounds. If combination of two inhibitors causes a greater than 10-fold reduction in minimum inhibitory concentration, minimum bactericidal concentrations of this combination can be determined and the combination can be tested in a mouse model study.

Inhibition of Mycobacterial Infection in Mice Using Inhibitors of Branched Chain Amino Acid Biosynthesis.

In the preliminary mouse model study, the colony forming units measured in the spleens and lungs was less than expected based on comparison with other studies (Klemens et al., 1994; Lalande et al., 1993). The most likely reason for this is that the bacteria used for infection were taken from the surface of an agar slant. The low infection rate may have resulted because of a high percentage of inviable cells on the surface of the agar medium (Brown, 1983). To prevent this problem in future studies, bacteria to be used for mouse infections can be cultured in Middlebrook 7H9 ADC liquid medium containing 0.05% Tween 80. The culture can be grown in a Cell-stir (Kontes) flask containing a suspended magnetic stir-bar that will maintain constant aeration of the culture. This method will help to maintain viability of the bacteria (Brown, 1983). After 10 days of growth, the culture can be centrifuged and cells can be suspended in medium containing 15% glycerol. This suspension can be divided into aliquots to be stored at--80° C. and colony forming units/ml of the frozen stock can be determined. Because glycerol is toxic to mice it must be removed from the cell preparation prior to injection. To remove glycerol, cells from one of the frozen stocks can be pelleted by centrifugation and suspended in phosphate buffered saline to a concentration of $5\times10^7$ colony forming units/ml. Clumps of bacteria can be disrupted immediately prior to intravenous injection by sonicating the suspension briefly with a Branson sonifier equipped with a cup horn and 0.2 ml of the suspension ($10^7$ colony forring units) can be injected into the tail vein of mice. The protocol for injections of inhibitor and determination of colony forming units in lungs and spleen can be as described above in the methods section of this application.

Inhibitors and combinations of inhibitors that have a low minimum inhibitory concentration (<5 μg/ml) and that are not toxic to mice can be tested for in vivo activity in mouse model studies. The experimental approach can be used initially to repeat the experiment using a dose of 500 mg/kg of sulfometuron methyl (FIG. 2) and to test the combination of 20 mg/kg sulfometuron methyl and 200 mg/kg N-isopropyloxayl hydroxamate. When new inhibitors are obtained, pilot studies can be performed with high doses of inhibitor to quickly identify potentially useful compounds. Inhibitors that are effective at high doses can be tested further in dose-response experiments to determine the minimum dosage required to inhibit growth of bacteria in vivo. For all studies, a control group of mice will receive 25 mg/kg isoniazid, which significantly reduced *Mycobacterium tuberculosis* in spleens and lungs of mice (Lalande et al., 1993).

Identification of Inhibitors that Reduce *Mycobacterium tuberculosis* Colony Forming Units in vivo To determine if injections of inhibitor reduces the number of bacteria in vivo, a group of infected "early control" mice can be added to the dose-response experiments described above. The early controls can be sacrificed on the day that inhibitor injections are started (day 5 after infection) and colony forming units in the spleens and lungs can be determined ("starting colony forming units"). Starting colony forming units can be compared with colony forming units determined at the end of the 30-day treatment ("final colony forming units"). If treatment with the inhibitor causes killing of *Mycobacterium tuberculosis* in vivo, then the final colony forming units can be lower than the starting colony forming units. If, on the other hand, the inhibitor simply prevents growth of the bacteria over the 30-day trial period, then the final colony forming units can be equivalent to the starting colony forming units. When similar comparisons were done with standard antimycobacterial drugs, isoniazid and rifampicin caused a decrease in final colony forming units, whereas pyrazinamide and ethambutol did not cause a decrease (Klemens et al., 1994). Of course, killing action of any of the drugs to be tested will presumably be aided by the immune system of the mouse (Brown, 1983).

TABLE 1

Minimum Inhibitory Concentratons of branched chain amino acid pathway inhibitors against *Mycobacterium tuberculosis*

| Inhibitor | Inhibitor target | inhibited step in pathway | strain tested | MIC ($\mu$g/ml) −LIV[a] | MIC ($\mu$g/ml) +LIV |
|---|---|---|---|---|---|
| SM | ALS | step 1 | RC1 | 0.3 | 1.8 |
| | | | ATCC35801 | 3.6 | >3.6 |
| Chlorsul-furon | ALS | step 1 | RC1 | 4.4 | >35 |
| | KARI | step 2 | RC1 | 9.2 | 9.2 |
| IpOHA | | | ATCC35801 | 18 | >18 |
| SM + IpOHA | ALS and KARI | step 1 and step 2 | ATCC35801 | <0.01SM <0.07 IpOHA | >3.6SM >18 IpOHA |

[a]LIV, leucine, isoleucine, and valine

TABLE 2

Minimum Inhibitory Concentratons of first-line anti-tuberculosis drugs[a]

| Drug | mode of action | target | MIC ($\mu$g/ml) |
|---|---|---|---|
| Isoniazid | inhibits mycolic acid synthesis | Enoyl-acyl carrier protein reductase[b] | 0.2 |
| Ethambutol | inhibits mycolic acid synthesis | ? | 2 |
| Pyrazinamide | inhibits mycolic acid synthesis | ? | 16 |
| Rifampicin | inhibits RNA synthesis | RNA polymerase | 0.5 |
| Streptomycin | inhibits protein synthesis | Ribosomal 30S subunit | 3 |

[a]Heifets L. B. (1994)
[b]Dressen et al. (1995)

TABLE 3

Kruskal-Wallis test for overall differences[a] between sample sets

| Sample set | Chi-square | degrees of freedom. | P |
|---|---|---|---|
| Spleen | 6.8 | 3 | 0.07 |
| Lung | 11.1 | 3 | 0.01 |

[a]$P < 0.05$ considered significant

TABLE 4

Mann-Whitney U test for significant differences[a] in colony forming units values measured in lungs

| groups compared | 2-tailed P |
|---|---|
| PBS and 20 mg SM/kg | 0.39 |
| PBS and 100 mg SM/kg | 0.65 |
| PBS and 500 mg SM/kg | 0.03 |
| 20 mg/kg and 100 mg SM/kg | 0.31 |
| 20 mg/kg and 500 mg SM/kg | 0.002 |
| 100 mg/kg and 500 mg SM/kg | 0.009 |

[a]$P < 0.05$ considered significant

Throughout this application, various publications have been referenced. The disclosures in these publications are incorporated herein by reference in order to more fully describe the state of the art.

References

Abell, L. M., Hanna, W. S., Kunitsky, K. J., and Kerschen, J. A. (1995). Active site inhibitors of acetolactate synthase. Pestic. Sci. 44, 89–92.

Allaudeen, H. S., and Ramakrishnan, T. (1971). Biosynthesis of Branched Chain Amino acids in *Mycobacterium tuberculosis* H37Rv III. Purification and properties of reductase and reductoisomerase. Indian Journal of Biochemistry and Biophysics 8, 23–27.

Allaudeen, H. S., and Ramakrishnan, T. (1970). Biosynthesis of isoleucine and valine in *Mycobacterium tuberculosis* H37Rv II. Purification and properties of acetohydroxy acid isomerase. Archives of Biochemistry and Biophysics 140, 245–256.

Allaudeen, H. S., and Ramakrishnan, T. (1968). Biosynthesis of isoleucine and valine in *Mycobacterium tuberculosis* H37Rv. Archives of Biochemistry and Biophysics 125, 199–209.

Aulabaugh, A., and Schloss, J. V. (1990). Oxalyl hydroxamates as reaction-intermediate analogues for ketol-acid reductoisomerase. Biochemistry 29, 2824–2830.

Aulabaugh, A., and Schloss, J. V. (1990). Oxalyl hydroxamates as reaction-intermediate analogues for ketol-acid reductoisomerase. Biochemistry 29, 2824–2830.

Aulabaugh, A. E., and Schloss, J. V. (1988). Preparation of oxalylhydroxamates as ketol-acid reductoisomerase-inhibiting herbicides and microbicides. Canadian Patent, Canada, CA 2002021 AA 900503 US 88-266968 881103.

Bloom, B. R., and Murray, C. J. L. (1992). Tuberculosis: commentary on a reemergent killer. Science 257, 1055–1064.

Brown, H. M., and Cotterman, J. C. (1994). Recent advances in sulfonylurea herbicides. In Chemistry of Plant Protection. Herbicides Inhibiting Branched-Chain Amino Acid Biosynthesis, J. Stetter, ed. (Berlin: Springer-Verlag), pp. 47–81.

Brown, I. N. (1983). Animal models and immune mechanisms in mycobacterial infection. In Biology of Mycobacteria, R. C. and J. Stanford, eds. (London: Academic Press), pp. 173–234.

Burrows, B. F., and Turner, W. B. (1966). 1-Amino-2-nitrocyclopentanecarboxylic acid. A new naturally-occurring nitro-compound. J. Chem. Soc. C, 255–260.

Collins, F. M. (1993). Tuberculosis: the return of an old enemy. Critical Rev. in Microbiol. 19, 1–16.

Dressen, A., Quemard, A., Blanchard, J. S., Jacobs, W. R. J., and Sacchettini, J. C. (1995). Crystal structure and Function of the isoniazid target of Mycobacterium tuberculosis. Science 267, 1638–1641.

Dunlap, N. E., and Kimerling, M. E. (1994). Drug-resistant tuberculosis in adults: implications for the health care worker. Infectious Agents and Dis. 3, 245–255.

Emptage, M. H. (1990). Yeast isopropylmalate isomerase as an iron-sulfur protein. In Biosynthesis of Branched Chain Amino Acids, Z. Barak, D. M. Chipman and J. V. Schloss, eds. (Weinheim: VCH), pp. 315–328.

Emptage, M. H., and Schloss, J. V. (1986). Inhibition of isopropylmalate isomerase by a reaction intermediate analog. Fed. Proc 45, 1536.

Falco, S. C., Chaleff, R. S., Dumas, K. S., LaRossa, R. A., Leto, K. J., Mauvais, C. J., Mazur, B. J., Ray, T. B., Schloss, J. V., and Yadav, N. S. (1985). Molecular biology of sulfonylurea herbicide activity. In Biotechnology Plant Sci.: Relevance Agric. Eighties, (Symp.), M. Zaitlin, P. R. Day and A. Hollaender, eds. (Orlando: Academic Press), pp. 313–328.

Flint, D. H., and Nudelman, A. (1993). Studies on the active site of dihydroxy-acid dehydratase. Bioorg. Chem. 21, 367–385.

Gee, S. K., and Hay, J. V. (1994). Recent developments in the chemistry of sulfonylurea herbicides. In Chemistry of Plant Protection. Herbicides Inhibiting Branched-Chain Amino Acid Biosynthesis, J. Stetter, ed. (Berlin: Springer-Verlag), pp. 15–46.

Hawkes, T. R., Cox, J. M., Fraser, T. E. M., and Lewis, T. (1993). A herbicidal inhibitor of isopropylmalate isomerase. Z. Naturforsch 48c, 364–368.

Hawkes, T. R., and Edwards, L. S. (1990). Inhibition of acetolactate isomeroreductase from Saccharomyces cerevisiae. In Biosynthesis of Branched Chain Amino Acids, Z. Barak, D. M. Chipman and J. V. Schloss, eds. (Weinheim: VCH), pp. 413–424.

Hawkes, T. R., Howard, J. L., and Poutin, S. F. (1989). Herbicides that inhibit the biosynthesis of branched-chain amino acids. In Herbicides in plant metabolism, A. D. Dodge, ed. (Cambridge: Cambridge University Press), pp. 113–137.

Heifets, L. B., Flory, M. A., and Lindholm-Levy, P. J. (1989). Does pyrazinoic acid as an active moiety of pyrazinamide have specific activity against Mycobacterium tuberculosis? Antimicrobial Agents Chemother. 33, 1252–1254.

Hutchins, P., and Hershfield, E. (1993). The epidemiology of tuberculosis in foreign-born in Canada and the United States. In Tuberculosis: a comprehensive international approach., L. B. Reichman and E. S. Hershfield, eds. (New York: Marcel Dekker), pp. 531–550.

Jacobs, R. F. (1994). Multiple-drug-resistant tuberculosis. Clin. Infect. Dis. 19, 1–10.

Klemens, S. P., Sharpe, C. A., Rogge, M. C., and Cynamon, M. H. (1994). Activity of levofloxacin in a murine model of tuberculosis. Antimicrob. Agents and Chemother 38, 1476–1479.

Lalande, V., Truffot-Pernot, C., Paccaly-Moulin, A., Grosset, J., and Ji, B. (1993). Powerful bactericidal activity of sparfloxacin (AT-4140) against Mycobacterium tuberculosis in mice. Anitmicrob. Agents Chemother 37, 407–413.

McAdam, R. A., Weisbrod, T. R., Martin, J., Scuderi, J. D., Brown, A. M., Cirillo, J. D., Bloom, B. R., and Jacobs, W. R. J. (1995). In vivo growth characteristics of leucine and methionine auxotrophic mutants of Mycobacterium bovis BCG generated by transposon mutagenesis. Infect. and Immun. 63, 1004–1012.

Mitscher, L. A. (1995). Some ruminations on the present and future roles of combinatorial and multiplex syntheses in medicinal chemistry. Chemtracts: Org. Chem. 8, 19–25.

Murray, P. R. (1995). Manual of Clinical Microbiology (Washington, D.C.: ASM Press).

Pirrung, M. C., Ha, H. J., and Holmes, C. P. (1989). Purification and inhibition of spinach a,β-dihydroxyacid dehydratase. J. Org. Chem. 54, 1543–1548.

Pirrung, M. C., Han, H., and Ludwig, R. T. (1994). Inhibitors of Thennus thermophilus isopropylmalate dehydrogenase. J. Org. Chem 59, 2430–2436.

Schloss, J. V. (1994). Recent advances in understanding the mechanism and inhibition of acetolactate synthase. In Chemistry of Plant Protection. Herbicides Inhibiting Branched-Chain Amino Acid Biosynthesis, J. Stetter, ed. (Berlin: Springer-Verlag), pp. 3–14.

Schloss, J. V., and Aulabaugh, A. (1990). Acetolactate synthase and ketol-acid reductoisomerase: a search for a reason and a reason for a search. In Biosynthesis of branched chain amino acids, D. C. Z. Barak, and J. V. Schloss, ed. (Weinheim, Federal Rep. of Germany: VCH), pp. 403–411.

Schloss, J. V., Ciskanik, L. M., and Van Dyk, D. E. (1988). Origin of the herbacide binding site of acetolactate synthase. Nature 331, 360–362.

Schloss, J. V., Magolda, R., and Emptage, M. (1988). Synthesis of α-isopropyl-malate, β-isopropylmalate, and dimethylcitraconate. Meth. Enzymol. 166, 92–96.

Schloss, J. V., and Van Dyk, D. E. (1988). Acetolactate synthase isozyme II of Salmonella typhimurium. Meth. Enzymol. 166, 445–454.

Schulz, A., Sponemann, P., Kocher, H., and Wengenmayer, F. (1988). The herbicidally active experimental compound 2-dimethylphosphinoyl-2-hydroxy acetic acid is a potent inhibitor of the enzyme acetolactate reductoisomerase. FEBS Letters 238, 375–378.

Schulz, A., and Taggeselle, P. (1990). The experimental herbacide 2-dimethylphosphinoyl-2-hydroxy acetic acid inhibits the biosynthesis of branched chain amino acids and pantoate in Klebsiella pneumoniae. In Biosynthesis of branched chain amino acids, D. C. Z. Barak, and J. V. Schloss, ed. (Weinheim, Federal Rep. of Germany: VCH).

Siegel, S. (1956). Nonparametric Statistics for the Behavioral Sciences (New York: McGraw Hill).

Silve, G., Valero-Guillen, P., Quemard, A., Dupont, M. A., Daffe, M., and Laneelle, G. (1993). Ethambutol inhibition of glucose metabolism in mycobacteria: a possible target of the drug. Antimicrob. Agents Chemother 37, 1536–1538.

Takayama, K., and Kilburn, J. O. (1989). Inhibition of synthesis of arabinogalactan by ethambutol in Mycobacterium smegmatis. Antimicrobial Agents and Chemotherapy 33, 1493–1499.

Tse, J. M.-T., and Schloss, J. V. (1993). The oxygenase reaction of acetolactate synthase. Biochemistry 32, 10398–10403.

Wittenbach, V. A., Aulabaugh, A., and Schloss, J. V. (1991). Examples of extraneous site inhibitors and reaction intermediate analogs: acetolactate synthase and ketol-acid reductoisomerase. In Pesticide Chemistry, H. Frehse, ed. (Weinheim: VCH).

Wittenbach, V. A., Rayner, D. R., and Schloss, J. V. (1992). Pressure points in the biosynthetic pathway for branched-chain amino acids. In Biosynthesis and molecular regulation of amino acids in plants, B. K. Singh, H. E. Flores and J. C. Shannon, eds.

Wittenbach, V. A., Teaney, P. W., Hanna, W. S., Rayner, D. R., and Schloss, J. V. (1994). Herbicidal activity of an isopropylmalate dehydrogenase inhibitor. Plant Physiol. 106, 321–328.

Wolucka, B. A., McNeil, M. R., de Hoffmann, E., Chojnacki, T., and Brennan, R. J. (1994). Recognition of the lipid intermediate for arabinogalactan/arabinomannan biosynthesis and its relation to the mode of action of ethambutol on mycobacteria. J. Biol. Chem. 269, 23328–23325.

Yajko, D. M., Madej, J. J., Lancaster, M. V., Sanders, C. A., Cawthon, V. L., Gee, B., Babst, A., and Hadley, W. K. (1995). Colorimitric method for determining minimum inhibitory concentrations of antimicrobial agents for *Mycobacterium tuberculosis*. J. Clin. Microbiol. 33, 2324–2327.

Zang, Y., and Young, D. B. (1993). Molecular mechanisms of isoniazid: a drug at the front line of tuberculosis control. Trends in Microbiology 1, 109–113.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A method for treating tuberculosis in a mammal which comprises administering to the mammal a therapeutically effective amount of an inhibitor compound that inhibits an enzyme in the branched chain amino acid biosynthetic pathway in *Mycobacterium tuberculosis*.

2. The method according to claim 1, wherein the inhibitor compound is an inhibitor of an enzyme selected from the group consisting of acetolactate synthase, ketol-acid reductoisomerase, dihydroxyacid dehydrogenase, isopropylmalate synthase, isopropylmalate isomerase, and isopropylmalate dehydrogenase.

3. The method according to claim 2, wherein the inhibitor compound is an inhibitor of an enzyme selected from the group consisting of acetolactate synthase, ketol-acid reductoisomerase, isopropylmalate isomerase, and isopropylmalate dehydrogenase.

4. The method according to claim 3, wherein the inhibitor compound is an inhibitor of acetolactate synthase.

5. The method according to claim 4, wherein the inhibitor is selected from the group consisting of sulfonylureas, imidazolinones, triazolopyrimidine sulfonanilides, and pyrimidyloxy salicylic acids.

6. The method according to claim 5, wherein the inhibitor is a sulfonylurea.

7. The method according to claim 6, wherein the inhibitor is sulfometuron methyl.

8. The method according to claim 1, wherein the inhibitor compound is present in an amount from about 1 mg/kg to about 500 mg/kg body weight.

9. The method according to claim 8, wherein the inhibitor compound is present in an amount from about 5 mg/kg to about 350 mg/kg body weight.

10. The method according to claim 7, wherein the inhibitor compound is sulfometuron methyl present in an amount from about 10 mg/kg to about 200 mg/kg body weight.

* * * * *